US 12,239,475 B2

(12) United States Patent
Shimizukawa et al.

(10) Patent No.: US 12,239,475 B2
(45) Date of Patent: Mar. 4, 2025

(54) RADIATION IMAGE DETECTOR COMPRISING A PLURALITY OF GATE CONTROL CIRCUITS, A PLURALITY OF READOUT CONTROL CIRCUITS, AND A POWER SUPPLY CIRCUIT

(71) Applicant: FUJIFILM CORPORATION, Tokyo (JP)

(72) Inventors: Sho Shimizukawa, Kanagawa (JP); Koji Yamamoto, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 148 days.

(21) Appl. No.: 18/055,838

(22) Filed: Nov. 16, 2022

(65) Prior Publication Data

US 2023/0168393 A1     Jun. 1, 2023

(30) Foreign Application Priority Data

Dec. 1, 2021   (JP) ................. 2021-195685

(51) Int. Cl.
*A61B 6/00*     (2024.01)
*A61B 6/42*     (2024.01)
(Continued)

(52) U.S. Cl.
CPC .......... *A61B 6/4283* (2013.01); *A61B 6/4208* (2013.01); *A61B 6/4233* (2013.01);
(Continued)

(58) Field of Classification Search
CPC ......... A61B 6/032; A61B 6/42; A61B 6/4208; A61B 6/4233; A61B 6/4241; A61B 6/4258; A61B 6/4266; A61B 6/4275; A61B 6/4283; G01T 1/17; G01T 1/175; G01T 1/2006; G01T 1/2018; G01T 1/20182;
(Continued)

(56) References Cited

U.S. PATENT DOCUMENTS 7,078,701 B2 *  7/2006  Ishii .................. G21K 4/00
                                            250/370.08
8,183,822 B2 *  5/2012  Tsubota ............. H02J 7/00047
                                            320/125
(Continued)

FOREIGN PATENT DOCUMENTS

WO     2019/004233 A1   1/2019

*Primary Examiner* — Allen C. Ho
(74) *Attorney, Agent, or Firm* — SOLARIS Intellectual Property Group, PLLC

(57) ABSTRACT

An electronic cassette has a detection panel (light detection substrate) in which pixels for accumulating electric charges corresponding to radiation are arranged. The electronic cassette includes two gate control circuits that control an operation of a gate drive circuit, a power supply circuit that supplies power to the gate control circuits, a first wiring line, and a second wiring line. The first wiring line connects the power supply circuit and each of two gate control circuits to each other, and supplies each of two gate control circuits with the power supplied from the power supply circuit. The second wiring line connects two gate control circuits to each other. The power supplied from the power supply circuit to one of two gate control circuits is diverted to the other, through the second wiring line.

7 Claims, 10 Drawing Sheets

(51) Int. Cl.
*G01T 1/17* (2006.01)
*G01T 1/175* (2006.01)
*G01T 1/20* (2006.01)
*G01T 1/24* (2006.01)
*G01T 1/29* (2006.01)

(52) U.S. Cl.
CPC .......... *A61B 6/4241* (2013.01); *A61B 6/4266* (2013.01); *G01T 1/17* (2013.01); *G01T 1/175* (2013.01); *G01T 1/20184* (2020.05); *G01T 1/247* (2013.01); *G01T 1/2928* (2013.01)

(58) Field of Classification Search
CPC ....... G01T 1/20184; G01T 1/24; G01T 1/243; G01T 1/247; G01T 1/29; G01T 1/2914; G01T 1/2928
USPC ............................. 250/370.09; 378/19, 98.8
See application file for complete search history.

(56) References Cited

U.S. PATENT DOCUMENTS

| | | | | |
|---|---|---|---|---|
| 8,358,740 B2* | 1/2013 | Nakatsugawa | ........ | A61B 6/586 378/116 |
| 8,362,437 B2* | 1/2013 | Tsubota | ................. | G01T 1/247 250/370.08 |
| 8,532,262 B2* | 9/2013 | Iwakiri | ................ | A61B 6/4233 378/108 |
| 8,546,777 B2* | 10/2013 | Utsunomiya | ............ | A61B 6/56 250/580 |
| 8,550,709 B2* | 10/2013 | Nishino | ................... | A61B 6/06 378/207 |
| 8,563,915 B2* | 10/2013 | Takenaka | ............. | H04N 25/677 348/241 |
| 8,591,106 B2* | 11/2013 | Nishino | ............... | A61B 6/4283 378/189 |
| 8,664,615 B2* | 3/2014 | Amitani | ................... | A61B 6/00 250/370.09 |
| 8,704,188 B2* | 4/2014 | Kitano | ................. | A61B 6/4405 250/370.09 |
| 8,750,455 B2* | 6/2014 | Kondou | ............. | G01T 1/20184 378/98.8 |
| 8,785,871 B2* | 7/2014 | Muraoka | ................. | H04N 1/41 250/370.09 |
| 8,785,876 B2* | 7/2014 | Tajima | ................. | A61B 6/4241 250/363.02 |
| 8,866,095 B2* | 10/2014 | Oguma | ..................... | G01T 1/16 250/370.11 |
| 9,020,097 B2* | 4/2015 | Iwakiri | ................ | A61B 6/4283 378/62 |
| 9,341,723 B2* | 5/2016 | Niekawa | ................ | G01T 1/244 |
| 9,360,561 B2* | 6/2016 | Takenaka | .................. | G01T 1/17 |
| 9,645,259 B2* | 5/2017 | Kameshima | ........... | H04N 23/30 |
| 9,668,331 B2* | 5/2017 | Takahashi | ............ | A61B 6/4233 |
| 9,778,380 B2* | 10/2017 | Enomoto | ............. | A61B 6/4233 |
| 9,826,946 B2* | 11/2017 | Ota | ....... | A61B 6/4233 |
| 10,440,290 B2* | 10/2019 | Kikuchi | ................... | H04N 5/32 |
| 10,488,534 B2* | 11/2019 | Kawaguchi | ............... | G01T 7/00 |
| 10,520,804 B2* | 12/2019 | Miyoshi | ............... | A61B 6/4283 |
| 10,524,746 B2 | 1/2020 | Maruta | ................ | A61B 6/4283 |
| 10,537,295 B2* | 1/2020 | Watanabe | ............ | A61B 6/4233 |
| 10,561,389 B2* | 2/2020 | Hiroshige | .............. | H04N 23/60 |
| 10,568,595 B2* | 2/2020 | Hosoki | ................... | H04N 23/30 |
| 10,605,747 B2* | 3/2020 | Ubukata | ............. | A61B 6/566 |
| 10,628,923 B2* | 4/2020 | Takagi | ................. | A61B 6/4266 |
| 10,754,047 B2* | 8/2020 | Shimizukawa | ........ | G01T 1/2006 |
| 10,762,384 B2* | 9/2020 | Ito | ........................ | A61B 6/5211 |
| 10,785,424 B2* | 9/2020 | Kanamori | .............. | H04N 25/76 |
| 10,838,079 B2* | 11/2020 | Shimizukawa | .......... | G01T 1/175 |
| 10,838,082 B2* | 11/2020 | Ushikura | ............... | H01L 27/146 |
| 10,881,366 B2* | 1/2021 | Taninai | ................ | A61B 6/4208 |
| 10,888,293 B2* | 1/2021 | Katsushima | ............. | G06T 5/50 |
| 10,898,148 B2* | 1/2021 | Taneda | ................ | A61B 6/4283 |
| 10,939,890 B2* | 3/2021 | Kuwata | ................ | A61B 6/4494 |
| 10,973,490 B2* | 4/2021 | Kawana | ................ | A61B 6/563 |
| 10,987,078 B2* | 4/2021 | Tsuji | .................... | A61B 6/5282 |
| 10,989,818 B2* | 4/2021 | Ushikura | .................. | G01T 1/24 |
| 10,992,885 B2* | 4/2021 | Iwakiri | ............... | A61B 6/4283 |
| 11,044,431 B2* | 6/2021 | Ota | ...... | G01T 1/20184 |
| 11,062,735 B2* | 7/2021 | Taneda | ................ | A61B 6/4405 |
| 11,064,966 B2* | 7/2021 | Iwakiri | ............... | A61B 6/4283 |
| 11,090,018 B2* | 8/2021 | Watanabe | ............ | A61B 6/4233 |
| 11,128,816 B2* | 9/2021 | Koeda | .................. | A61B 6/5205 |
| 11,185,303 B2* | 11/2021 | Kuwabara | ............. | G01T 1/2006 |
| 11,206,366 B2* | 12/2021 | Iwakiri | ................ | A61B 6/4233 |
| 11,313,979 B2* | 4/2022 | Shimizukawa | ...... | A61B 6/4233 |
| 11,368,640 B2* | 6/2022 | Ofuji | ..................... | H04N 25/78 |
| 11,382,579 B2* | 7/2022 | Shimizukawa | ........ | A61B 6/461 |
| 11,415,715 B2* | 8/2022 | Iwakiri | ..................... | A61B 6/00 |
| 11,520,057 B2* | 12/2022 | Iwakiri | ..................... | G01T 1/17 |
| 11,612,366 B2* | 3/2023 | Ushikura | ................ | G01T 1/244 378/62 |
| 11,624,716 B2* | 4/2023 | Ushikura | ................ | G01N 23/04 378/62 |
| 11,701,080 B2* | 7/2023 | Koeda | .................... | H04N 25/40 378/98 |
| 11,735,622 B2* | 8/2023 | Ushikura | .................. | G01T 1/20 250/475.2 |
| 11,747,492 B2* | 9/2023 | Horiuchi | ............. | A61B 6/4283 250/369 |
| 11,766,227 B2* | 9/2023 | Ushikura | .................. | G01T 1/20 250/336.1 |
| 11,852,759 B2* | 12/2023 | Narukawa | ............. | G01T 1/2002 |
| 11,860,323 B2* | 1/2024 | Kyushima | ......... | H01L 27/14618 |
| 11,877,875 B2* | 1/2024 | Ushikura | ................ | G01T 1/20 |
| 2020/0132864 A1 | 4/2020 | Shimizukawa et al. | | |

* cited by examiner

⟨WHEN GATE DRIVE CIRCUITS IN UPPER HALF ARE IN OPERATION⟩

<WHEN GATE DRIVE CIRCUITS IN LOWER HALF ARE IN OPERATION>

RADIATION IMAGE DETECTOR COMPRISING A PLURALITY OF GATE CONTROL CIRCUITS, A PLURALITY OF READOUT CONTROL CIRCUITS, AND A POWER SUPPLY CIRCUIT

CROSS-REFERENCE TO RELATED APPLICATIONS

The present application claims priority under 35 U.S.C. § 119 to Japanese Patent Application No. 2021-195685, filed on Dec. 1, 2021. The above application is hereby expressly incorporated by reference, in its entirety, into the present application.

BACKGROUND

1. Technical Field

The technology of the present disclosure relates to a radiation image detector.

2. Description of the Related Art

A radiation image detector having a detection panel in which pixels for accumulating electric charges corresponding to radiation are arranged is known. The detection panel is also called a flat panel detector (FPD). The radiation image detector incorporates various circuits, such as a gate drive circuit, a gate control circuit that controls an operation of the gate drive circuit, a readout circuit, a readout control circuit that controls an operation of the readout circuit, and a power supply circuit that supplies power to these circuits. The gate drive circuit is a circuit that applies, to a switching element of the pixel, a gate pulse for reading out the electric charge from the pixel. The readout circuit is a circuit that converts the electric charge from the pixel into an analog voltage signal and that converts the analog voltage signal into a digital signal to output the digital signal as a radiation image.

WO2019/004233A discloses a radiation image detector having a plurality of gate drive circuits and a plurality of readout circuits. The plurality of gate drive circuits each share a group of rows (for example, 240 rows obtained by equally dividing 2880 rows by 12) obtained by equally dividing rows of pixels of a detection panel. Similarly, the plurality of readout circuits each share a group of columns (for example, 144 columns obtained by equally dividing 2304 columns by 16) obtained by equally dividing columns of the pixels of the detection panel.

SUMMARY

In a case where the plurality of gate drive circuits and the plurality of readout circuits are provided as in WO2019/004233A, a plurality of control circuits (a plurality of gate control circuits or a plurality of readout control circuits may share the operation control of the plurality of gate drive circuits or the plurality of readout circuits, in order to reduce the control burden. For example, in a case where two control circuits share the operation control of the plurality of gate drive circuits, a control circuit that is in charge of gate drive circuits in an upper half of the rows of the pixels of the detection panel and a control circuit that is in charge of gate drive circuits in a lower half thereof are provided. In a case where the plurality of control circuits are provided in this way, power supply may become unstable because power is supplied from the power supply circuit to each of the plurality of control circuits.

One embodiment according to the technology of the present disclosure provides a radiation image detector capable of stably supplying power to a plurality of control circuits.

According to the present disclosure, there is provided a radiation image detector having a detection panel in which pixels for accumulating electric charges corresponding to radiation are arranged, the radiation image detector comprising: a plurality of control circuits that control an operation of the detection panel; a power supply circuit that supplies power to the plurality of control circuits; a first wiring line that connects the power supply circuit and each of the plurality of control circuits to each other and is used to supply each of the plurality of control circuits with the power supplied from the power supply circuit; and at least one second wiring line that connects at least two control circuits to each other, among the plurality of control circuits.

It is preferable that the control circuit has a first power receiving terminal to which the first wiring line is connected, and a second power receiving terminal to which the second wiring line is connected, and the first power receiving terminal and the second power receiving terminal are connected to each other in series.

It is preferable that the radiation image detector has a rectangular shape in a plan view and has a long side having a length longer than 431.8 mm.

It is preferable that a length of one second wiring line is shorter than a total length of the first wiring lines.

It is preferable that the second wiring line is directly connected to the control circuit without a connecting component.

It is preferable that the control circuit is mounted on a flexible board.

It is preferable that the control circuit is a gate control circuit that controls an operation of a gate drive circuit which applies, to a switching element of the pixel, a gate pulse for reading out the electric charge from the pixel.

According to the technology of the present disclosure, it is possible to provide a radiation image detector capable of stably supplying power to a plurality of control circuits.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
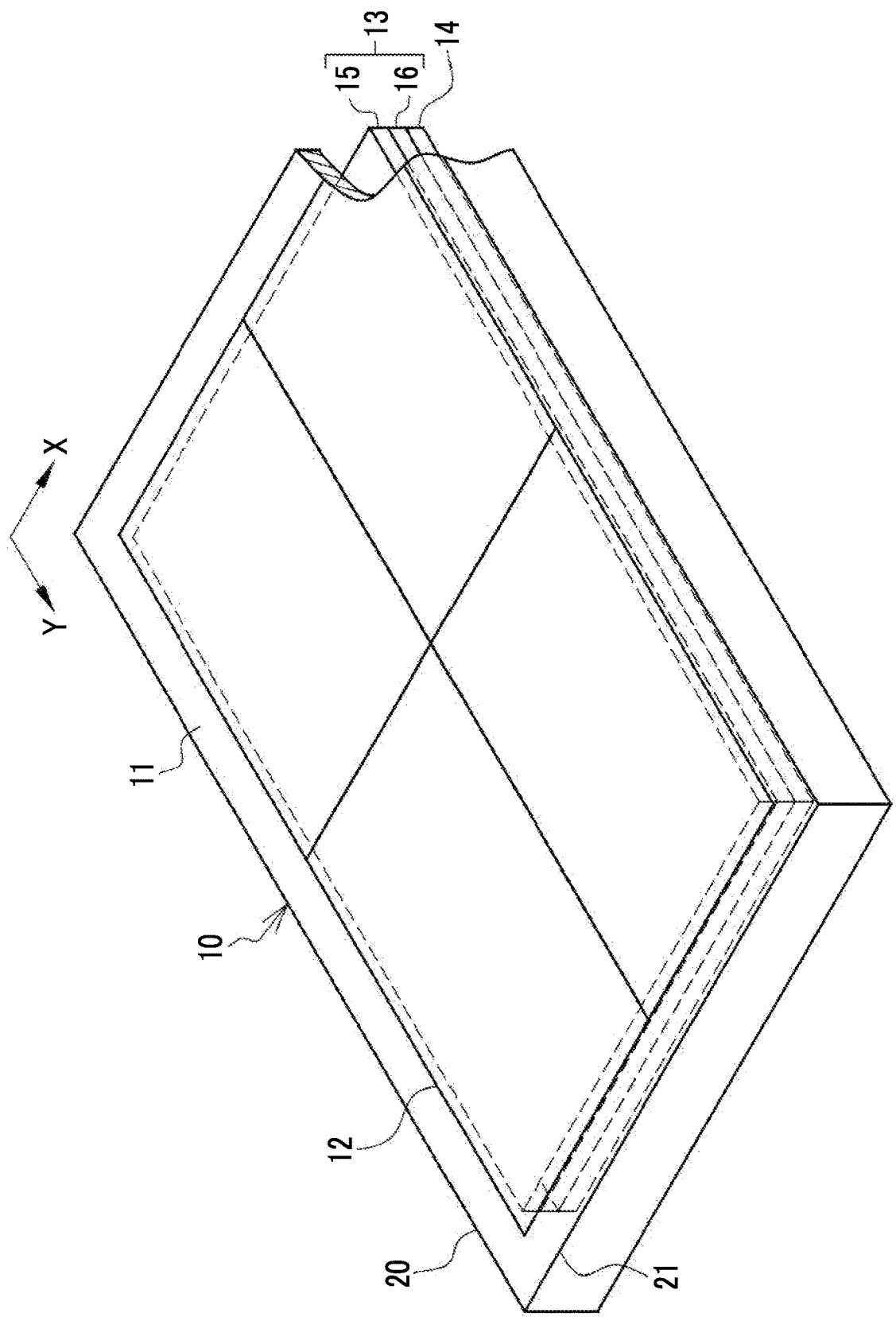
FIG. 1 is a perspective view of an electronic cassette.

As shown in FIG. 1 as an example, an electronic cassette 10 is a portable radiation image detector that outputs a radiation image corresponding to radiation which has passed through a subject. The electronic cassette 10 is used by being housed in a holder of an imaging table provided in a radiation imaging room of a medical facility. Further, the electronic cassette 10 can also be used by being removed from the holder of the imaging table and held by the subject, or by being inserted under the subject lying on a bed in a hospital room. The electronic cassette 10 is an example of the "radiation image detector" according to the technology of the present disclosure.

The electronic cassette 10 has a flat box-shaped (rectangular in a plan view) housing 11. The housing 11 is formed of a conductive metal or resin. Therefore, the housing 11 also functions as an electromagnetic shield for preventing electromagnetic noise from entering the electronic cassette 10 and electromagnetic noise from radiating from the electronic cassette 10 to the outside. A rectangular plate-shaped radiation transmission plate 12 that is slightly smaller than the housing 11 is attached to the front surface of the housing 11 on which radiation is incident. The radiation transmission plate 12 is formed of, for example, a carbon material that is lightweight, highly rigid, and highly radiolucent.

A detection panel 13 is housed in the housing 11. The detection panel 13 is attached to a rectangular plate-shaped base 14 made of metal. The detection panel 13 is composed of a scintillator 15 and a light detection substrate 16 having approximately the same size as the radiation transmission plate 12.

The scintillator 15 and the light detection substrate 16 are laminated in the order of the scintillator 15 and the light detection substrate 16 when viewed from the front surface side of the housing 11 on which radiation is incident. The scintillator 15 has a phosphor, such as thallium-activated cesium iodide (CsI:Tl) or terbium-activated gadolinium oxysulfide (GOS, $Gd_2O_2S$:Tb), and converts the incident radiation into visible light to emit the visible light. The light detection substrate 16 has a configuration in which a plurality of pixels 60 (see FIG. 9) are arranged on a single thin film transistor (TFT) active matrix substrate, and detects the visible light emitted from the scintillator 15 to convert the visible light into an electrical signal.

The scintillator 15 and the light detection substrate 16 may be laminated in the order of the light detection substrate 16 and the scintillator 15 when viewed from the front surface side. Further, the detection panel 13 may be a direct conversion type detection panel that directly converts radiation into an electrical signal, instead of an indirect conversion type detection panel that converts radiation converted into visible light by the scintillator 15 of this example into an electrical signal in the light detection substrate 16.

Although not shown, the housing 11 incorporates a battery and an antenna. In a case where wireless communication with an external device is performed using the antenna, the electronic cassette 10 can be driven by power from the battery and used wirelessly.

Figure 2:
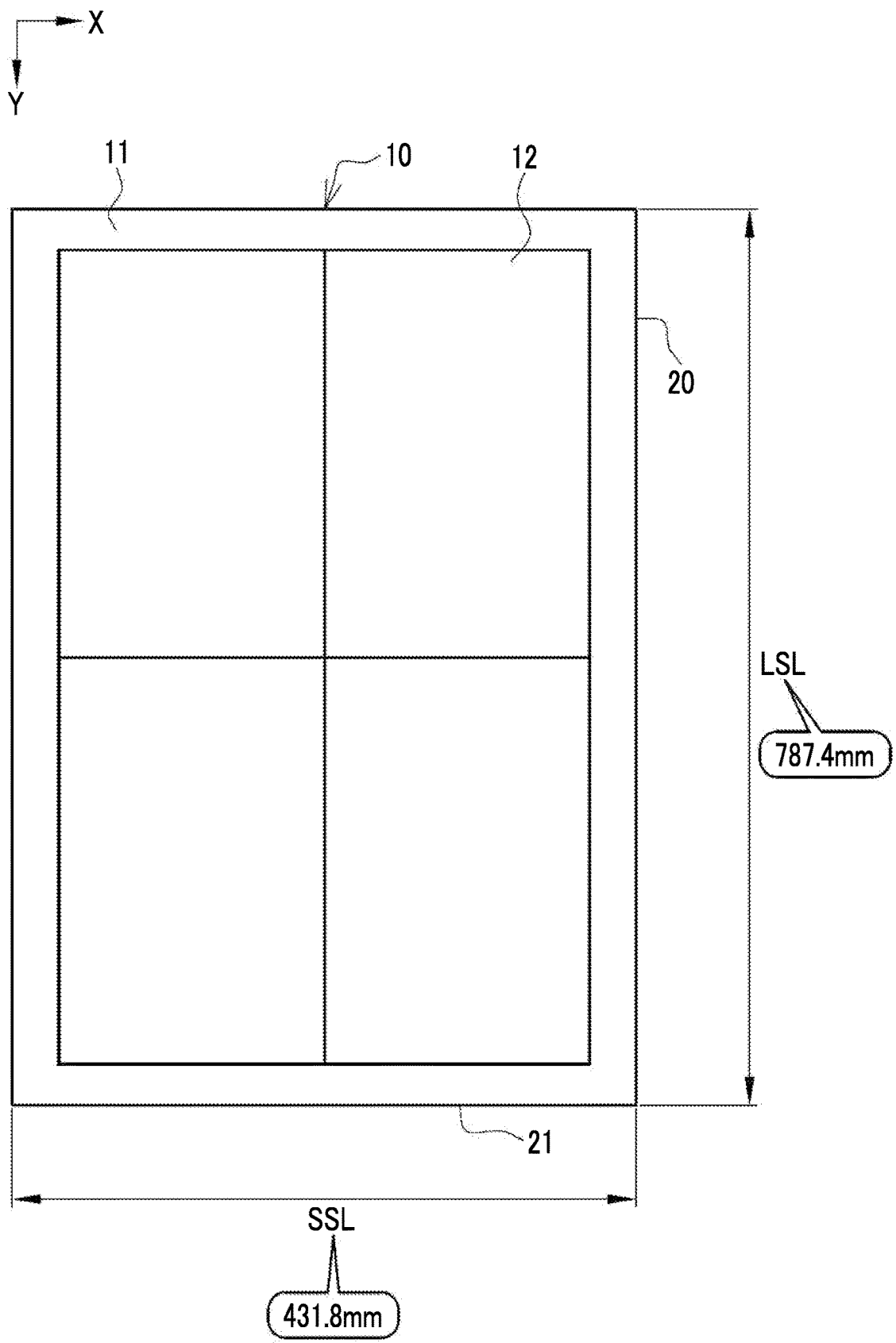
FIG. 2 is a plan view of the electronic cassette.

As shown in FIG. 2 as an example, a length LSL of a long side 20 of the housing 11 is, for example, 787.4 mm (≈31 inches). On the other hand, a length SSL of a short side 21 of the housing 11 is, for example, 431.8 mm (≈17 inches). That is, the length LSL of the long side 20 is longer than 431.8 mm.

Figure 3:
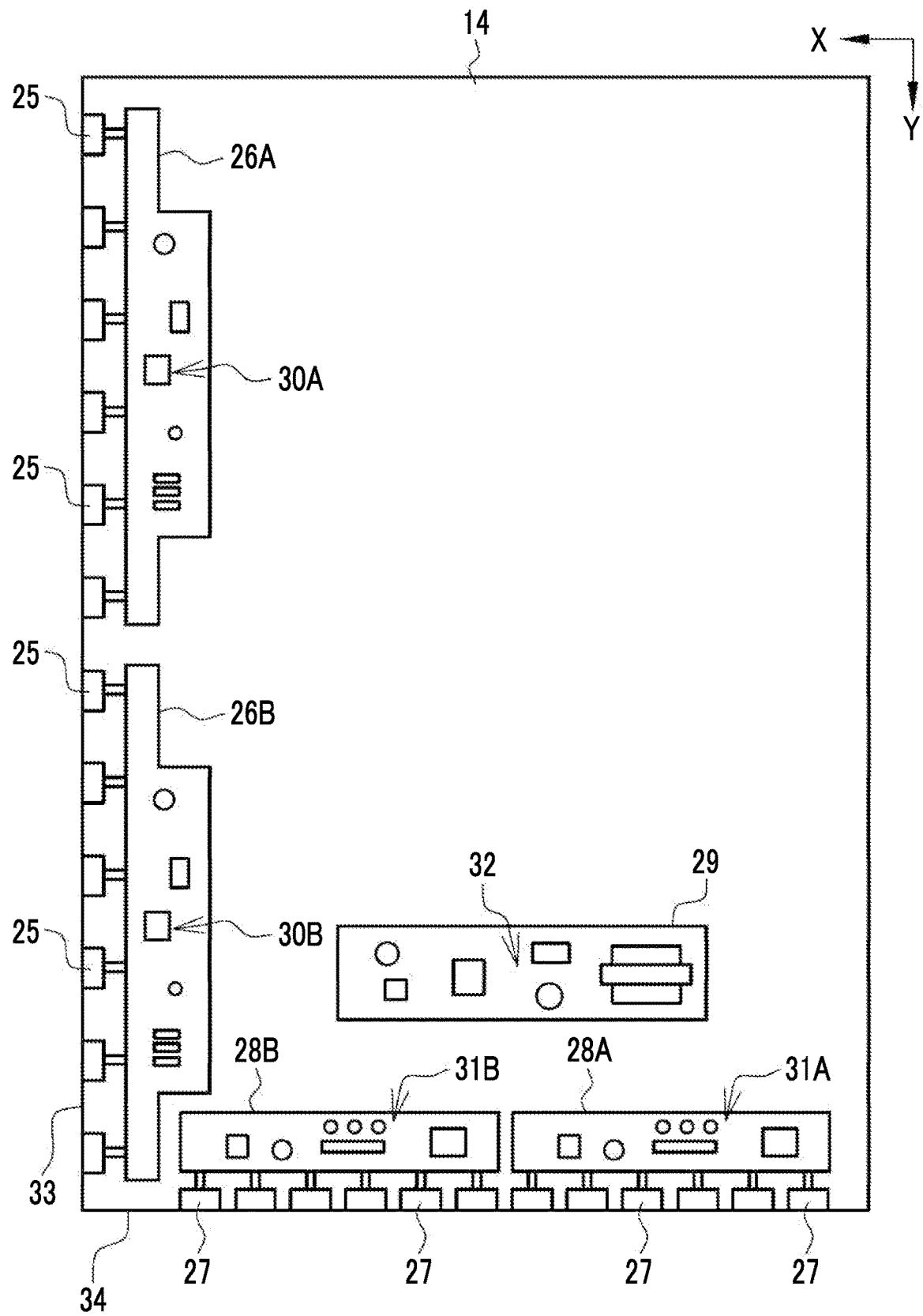
FIG. 3 is a diagram showing various circuit boards attached to a back surface of a base.

As shown in FIG. 3 as an example, a gate drive circuit 25, a gate control circuit board 26A, a gate control circuit board 26B, a readout circuit 27, a readout control circuit board 28A, a readout control circuit board 28B, and a power supply circuit board 29 are attached to the back surface of the base 14. A gate control circuit 30A is mounted on the gate control circuit board 26A, and a gate control circuit 30B is mounted on the gate control circuit board 26B. A readout control circuit 31A is mounted on the readout control circuit board 28A, and a readout control circuit 31B is mounted on the readout control circuit board 28B. A power supply circuit 32 is mounted on the power supply circuit board 29. Ground terminals (not shown) of the gate control circuit 30A, the gate control circuit 30B, the readout control circuit 31A, the readout control circuit 31B, and the power supply circuit 32 are connected to the base 14. In the following description, the gate control circuits 30A and 30B may be collectively referred to as a gate control circuit 30. Similarly, the readout control circuits 31A and 31B may be collectively referred to as a readout control circuit 31.

The gate drive circuit 25 is a circuit that applies, to a TFT 62 (see FIG. 9) of the pixel 60, a gate pulse for reading out an electric charge from the pixel 60. The gate drive circuit 25 is an integrated circuit (IC). A plurality of the gate drive circuits 25, here 12, are arranged on one of two long sides 33 of the base 14 at an equal interval.

The gate control circuit boards 26A and 26B are attached at positions closer to the side of the long side 33 on which the gate drive circuits 25 are arranged. Six gate drive circuits 25 in the upper half of the long side 33 are connected to the gate control circuit board 26A. The gate control circuit 30A controls the operations of six gate drive circuits 25 in the upper half. On the other hand, six gate drive circuits 25 in the lower half of the long side 33 are connected to the gate control circuit board 26B. The gate control circuit 30B controls the operations of six gate drive circuits 25 in the lower half. In a case where one party of six gate drive circuits 25 in the upper half and six gate drive circuits 25 in the lower half, that is, one of the gate control circuits 30A and 30B, operates, the other party does not operate. More specifically, the gate control circuit 30B does not operate in a case where six gate drive circuits 25 in the upper half are operated by the gate control circuit 30A, and the gate control circuit 30A does not operate in a case where six gate drive circuits 25 in the lower half are operated by the gate control circuit 30B.

The readout circuit 27 is a circuit that converts an electric charge from the pixel 60 into an analog voltage signal and that converts the analog voltage signal into a digital signal to output the digital signal as a radiation image. The readout circuit 27 is also the same integrated circuit as the gate drive circuit 25. Twelve readout circuits 27 are provided as in the gate drive circuits 25 and are arranged on one of two short sides 34 of the base 14 at an equal interval.

The readout control circuit boards 28A and 28B are attached at positions closer to the side of the short side 34 on which the readout circuits 27 are arranged. Six readout circuits 27 in the right half of the short side 34 (the left half when viewed from the front surface side of the base 14) are connected to the readout control circuit board 28A. The readout control circuit 31A controls the operations of six readout circuits 27 in the right half. On the other hand, six readout circuits 27 in the left half of the short side 34 (the right half when viewed from the front surface side of the base 14) are connected to the readout control circuit board 28B. The readout control circuit 31B controls the operations of six readout circuits 27 in the left half. Unlike the case of the gate drive circuit 25, six readout circuits 27 in the right half and six readout circuits 27 in the left half, that is, the readout control circuits 31A and 31B, operate at the same time.

The power supply circuit board 29 is attached at a position on the right side of the gate control circuit board 26B and on the upper side of the readout control circuit boards 28A and 28B. The power supply circuit 32 supplies power to each of the circuits 25, 27, 30A, 30B, 31A, and 31B.

Figure 4:
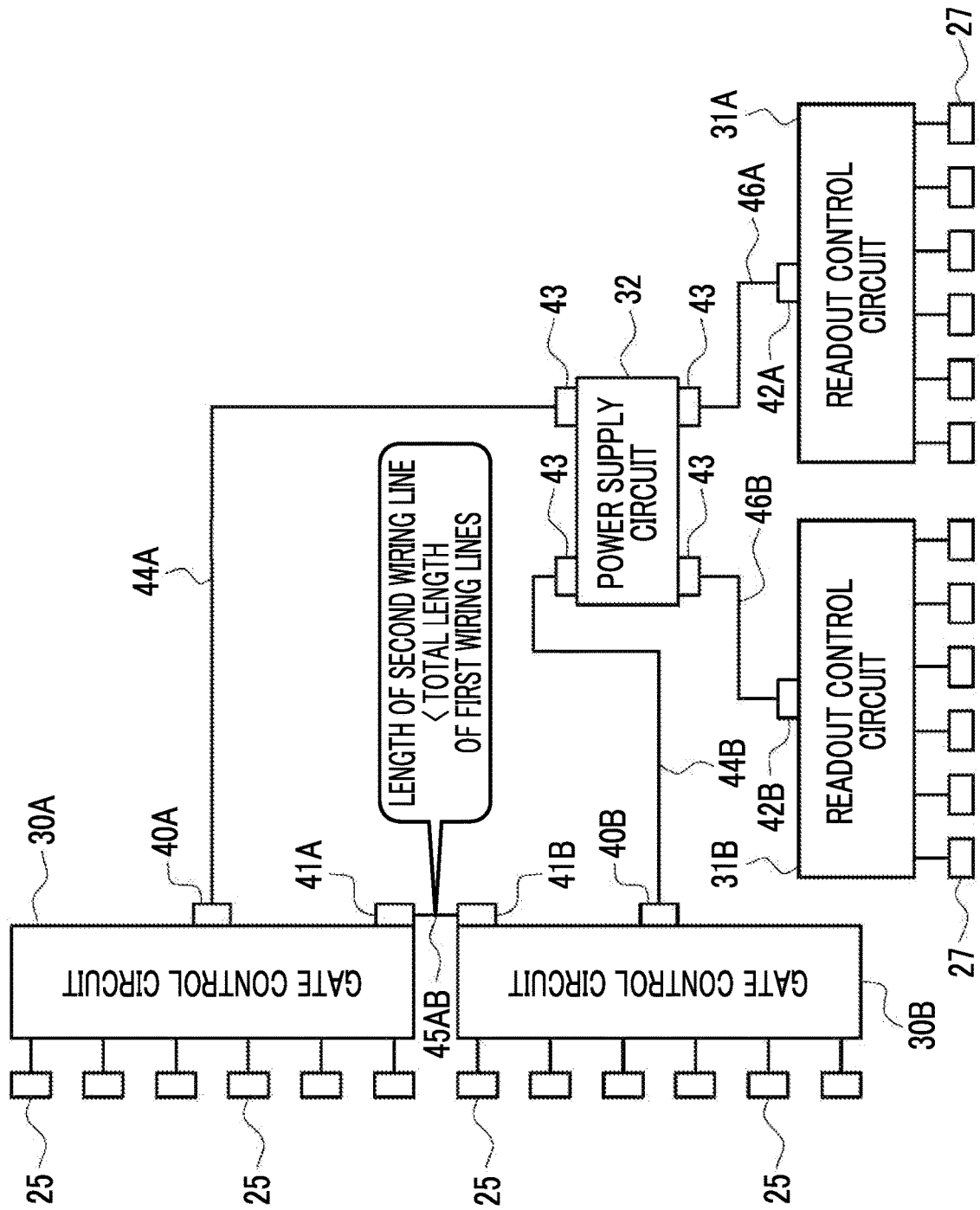
FIG. 4 is a diagram showing a connection relationship between various circuits.

As shown in FIG. 4 as an example, the gate control circuit 30A has a first power receiving terminal 40A and a second power receiving terminal 41A. The gate control circuit 30B has a first power receiving terminal 40B and a second power receiving terminal 41B. The readout control circuit 31A has a power receiving terminal 42A, and the readout control circuit 31B has a power receiving terminal 42B. The power supply circuit 32 has four power supply terminals 43.

One end of a first wiring line 44A is connected to the first power receiving terminal 40A of the gate control circuit 30A. The other end of the first wiring line 44A is connected to the power supply terminal 43 of the power supply circuit 32. Similarly, one end of a first wiring line 44B is connected to the first power receiving terminal 40B of the gate control circuit 30B. The other end of the first wiring line 44B is connected to the power supply terminal 43 of the power supply circuit 32. Power from the power supply circuit 32 is supplied to the gate control circuit 30A and the gate drive circuits 25 through the first wiring line 44A. Power from the power supply circuit 32 is supplied to the gate control circuit 30B and the gate drive circuits 25 through the first wiring line 44B.

One end of a second wiring line 45AB is connected to the second power receiving terminal 41A of the gate control circuit 30A. The other end of the second wiring line 45AB is connected to the second power receiving terminal 41B of the gate control circuit 30B. That is, the gate control circuits 30A and 30B are connected by the second wiring line 45AB. The length of the second wiring line 45AB is sufficiently shorter than the total length of the first wiring lines 44A and 44B. The second power receiving terminal 41A of the gate control circuit 30A and the second power receiving terminal 41B of the gate control circuit 30B are provided at end parts of the gate control circuits 30A and 30B, which face each other, in order to minimize the length of the second wiring line 45AB. The gate control circuit 30A and the gate control circuit 30B are an example of the "control circuit" according to the technology of the present disclosure.

One end of a wiring line 46A is connected to the power receiving terminal 42A of the readout control circuit 31A. The other end of the wiring line 46A is connected to the power supply terminal 43 of the power supply circuit 32. Similarly, one end of a wiring line 46B is connected to the power receiving terminal 42B of the readout control circuit 31B. The other end of the wiring line 46B is connected to the power supply terminal 43 of the power supply circuit 32. Power from the power supply circuit 32 is supplied to the readout control circuit 31A and the readout circuits 27 through the wiring line 46A. Power from the power supply circuit 32 is supplied to the readout control circuit 31B and the readout circuits 27 through the wiring line 46B.

Figure 5:
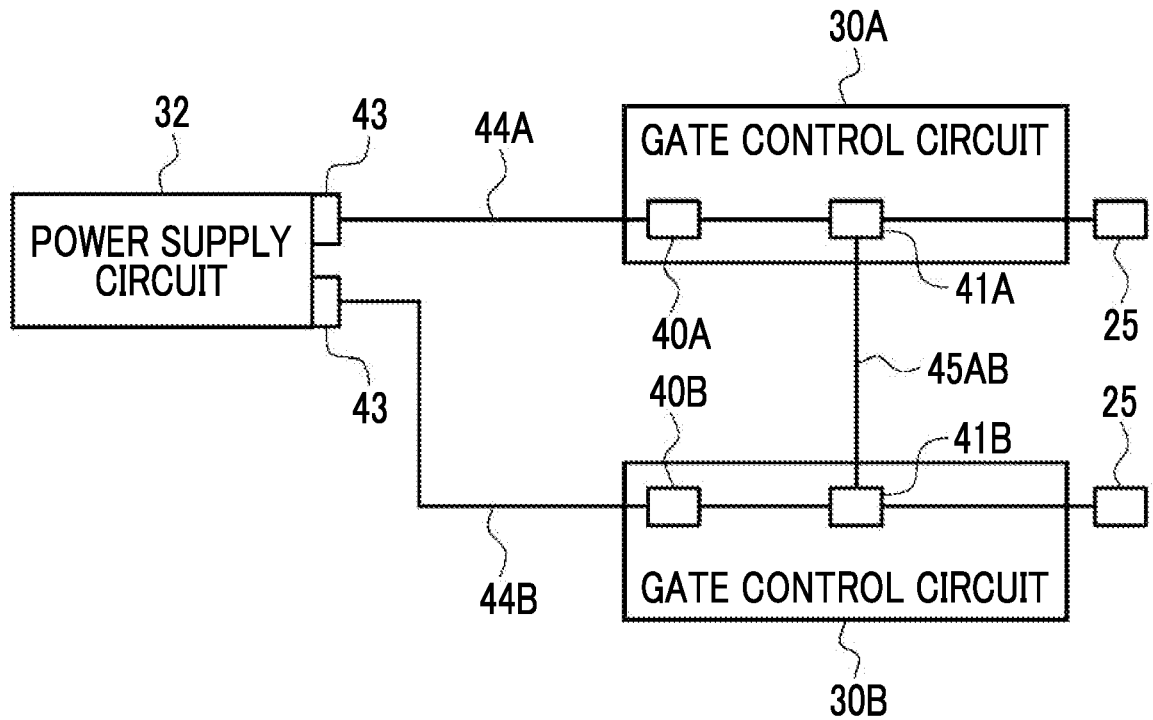
FIG. 5 is a diagram showing a connection relationship between a power supply circuit and a gate control circuit.
Figure 6:
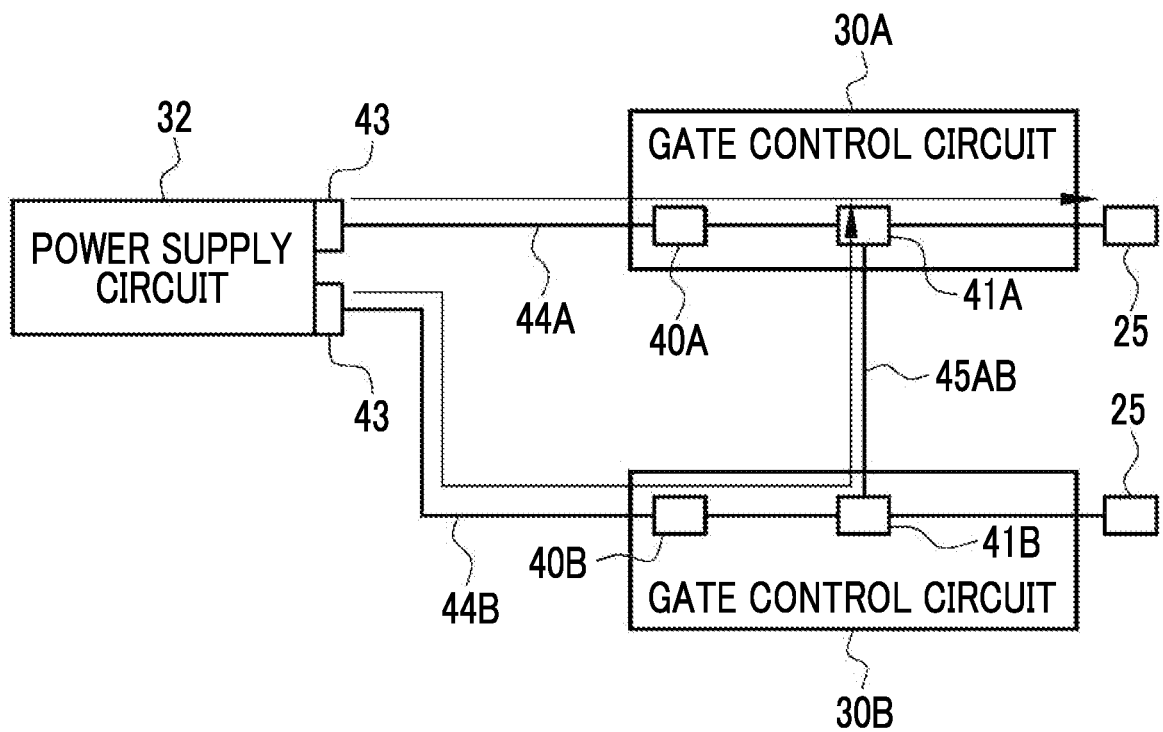
FIG. 6 is a diagram showing a flow of power when gate drive circuits in an upper half are in operation.
Figure 7:
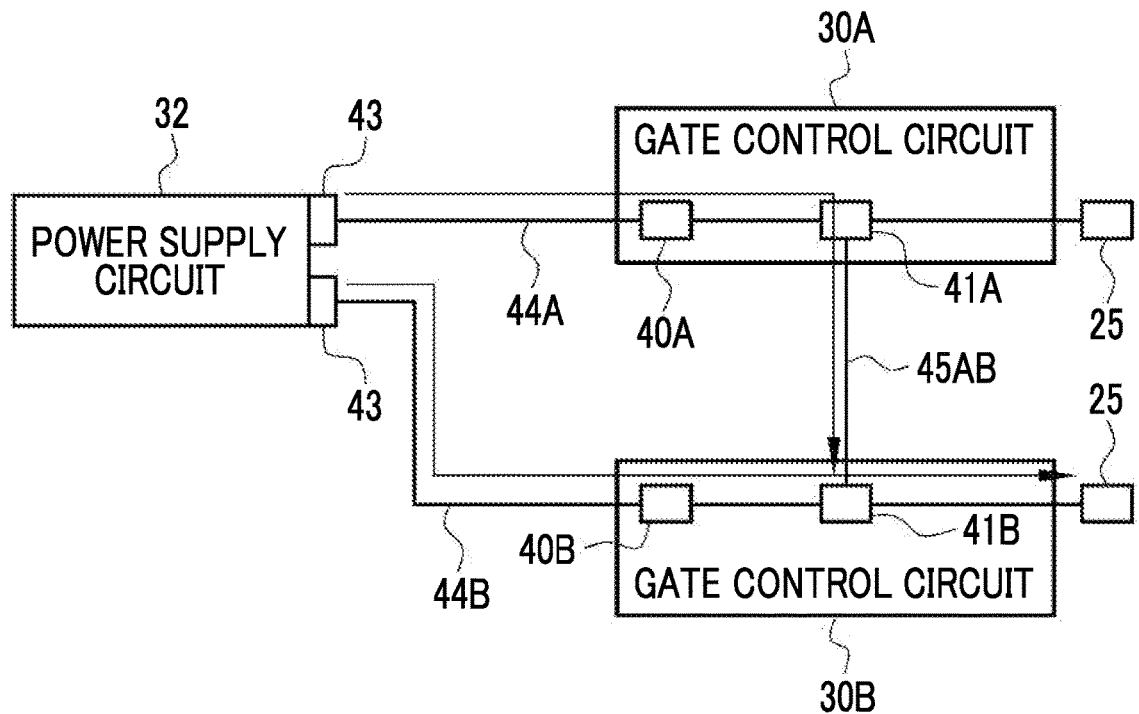
FIG. 7 is a diagram showing a flow of power when gate drive circuits in a lower half are in operation.

As shown in FIG. 5 as an example, in the gate control circuit 30A, the first power receiving terminal 40A and the second power receiving terminal 41A are connected to each other in series. Similarly, in the gate control circuit 30B, the first power receiving terminal 40B and the second power receiving terminal 41B are connected to each other in series. Therefore, as shown in FIG. 6 as an example, when the gate drive circuits 25 in the upper half are in operation, that is, when the gate control circuit 30A is in operation, the power supplied from the power supply circuit 32 to the gate control circuit 30B is diverted to the gate control circuit 30A via the second wiring line 45AB. On the contrary, as shown in FIG. 7 as an example, when the gate drive circuits 25 in the lower half are in operation, that is, when the gate control circuit 30B is in operation, the power supplied from the power supply circuit 32 to the gate control circuit 30A is diverted to the gate control circuit 30B via the second wiring line 45AB.

Figure 8:
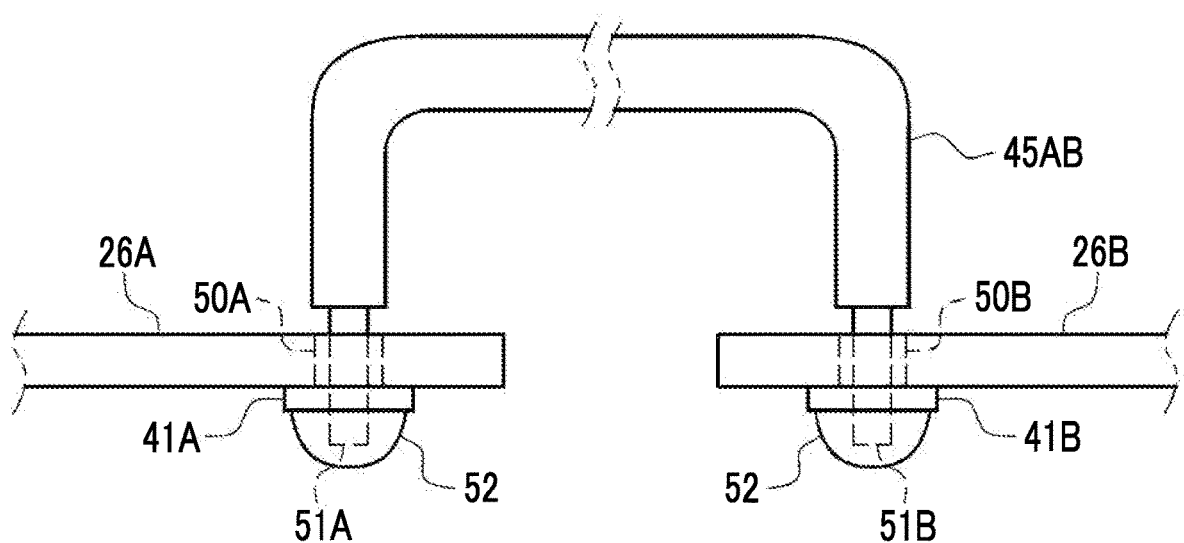
FIG. 8 is a diagram showing a connection method between a second wiring line and a second power receiving terminal.

As shown in FIG. 8 as an example, the gate control circuit board 26A is provided with an insertion hole 50A passing through the second power receiving terminal 41A. Similarly, the gate control circuit board 26B is provided with an insertion hole 50B passing through the second power receiving terminal 41B. A conductive wire 51A provided at one end of the second wiring line 45AB is inserted into the insertion hole 50A. A conductive wire 51B provided at the other end of the second wiring line 45AB is inserted into the insertion hole 50B. The conductive wire 51A is electrically connected to the second power receiving terminal 41A by a solder 52. Similarly, the conductive wire 51B is electrically connected to the second power receiving terminal 41B by the solder 52. That is, the second wiring line 45AB is a jumper wire that interconnects the second power receiving terminals 41A and 41B, and is directly connected to the gate control circuits 30A and 30B without a connecting component, such as a connector. Instead of the solder 52, a conductive paste, such as a silver paste, may be used to connect the conductive wire 51A and the second power receiving terminal 41A, and the conductive wire 51B and the second power receiving terminal 41B.

Figure 9:
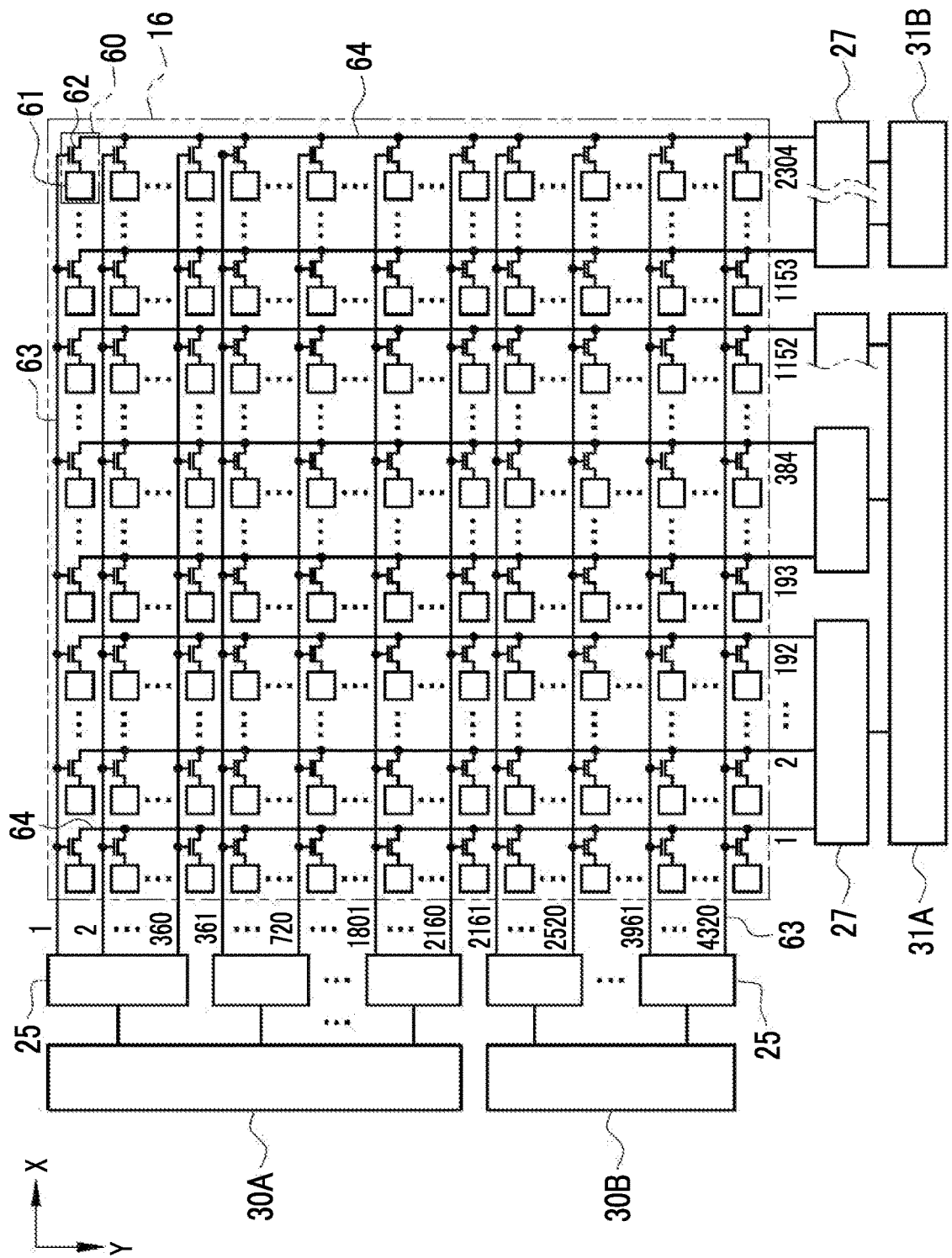
FIG. 9 is a diagram showing a configuration of a light detection substrate.

As shown in FIG. 9 as an example, the light detection substrate 16 has a configuration in which the plurality of pixels 60 are arranged in a two-dimensional matrix along an X direction and a Y direction orthogonal to each other. The X direction is a direction along the short sides 21 and 34, and the Y direction is a direction along the long sides 20 and 33. In a case where the number of pixels 60 arranged in the X direction is denoted by M and the number of pixels 60 arranged in the Y direction is denoted by N, M and N are each an integer of 2 or more, and for example, M=2304 and N=4320. As is well known, the pixel 60 has a photoelectric conversion unit 61 that generates an electric charge (electron-hole pairs) upon incidence of visible light and that accumulates the electric charge, and the TFT 62 serving as the switching element that controls the accumulation of the electric charge in the photoelectric conversion unit 61 and the readout of the electric charge from the photoelectric conversion unit 61. The photoelectric conversion unit 61 has, for example, a P-Intrinsic-N (PIN) type semiconductor layer, an upper electrode disposed on the upper side of the semiconductor layer, and a lower electrode disposed on the lower side of the semiconductor layer. A bias voltage is applied to the upper electrode. The lower electrode is connected to the drain electrode of TFT 62.

N scanning lines 63 extending parallel to the X direction and M signal lines 64 extending parallel to the Y direction are formed on the light detection substrate 16. N scanning lines 63 and M signal lines 64 are wired in a lattice form. The pixel 60 is disposed at an intersection portion of the scanning line 63 and the signal line 64. Specifically, in the pixel 60, a gate electrode of the TFT 62 is connected to the scanning line 63 and a source electrode of the TFT 62 is connected to the signal line 64. Each scanning line 63 is commonly connected to M pixels 60 for one row along the X direction. Each signal line 64 is commonly connected to N pixels 60 for one column along the Y direction. The scanning line 63 is connected to the gate drive circuit 25. The signal line 64 is connected to the readout circuit 27.

Twelve gate drive circuits 25 each share a group of rows obtained by equally dividing the rows of the pixels 60, here 360 rows obtained by equally dividing 4320 rows by 12. For example, among six gate drive circuits 25 connected to the gate control circuit 30A, the scanning lines 63 of the 1st to 360th rows are connected to the first gate drive circuit 25, and the scanning lines 63 of the 361st to 720th rows are connected to the second gate drive circuit 25. Further, among six gate drive circuits 25 connected to the gate control circuit 30B, the scanning lines 63 of the 2161st to 2520th rows are connected to the first gate drive circuit 25, and the scanning lines 63 of the 3961st to 4320th rows are connected to the sixth gate drive circuit 25. That is, one gate drive circuit 25 is in charge of reading out electric charges from the pixels 60 of 360 rows.

Twelve readout circuits 27 each share a group of columns obtained by equally dividing the columns of the pixels 60, here 192 columns obtained by equally dividing 2304 columns by 12. For example, among six readout circuits 27 connected to the readout control circuit 31A, the signal lines 64 of the 1st to 192nd columns are connected to the first readout circuit 27, and the signal lines 64 of the 193rd to 384th columns are connected to the second readout circuit 27. That is, one readout circuit 27 is in charge of converting electric charges from the pixels 60 of 192 columns into digital signals.

The gate drive circuits 25 output gate pulses to the scanning lines 63 under the control of the gate control circuits 30A and 30B. The gate pulses are uniformly applied to the gate electrodes of all the TFTs 62 of M pixels 60 connected to the scanning line 63. The TFT 62 is turned on in a case where the voltage of the gate pulse is at a high level, and is turned off in a case where the voltage of the gate pulse is at a low level. The time when the TFT 62 is turned on is defined by the pulse width of the gate pulse. The electric charges accumulated in the photoelectric conversion unit 61 of the pixel 60 are input to the readout circuit 27 through the signal line 64 in a case where the TFT 62 is turned on.

Figure 10:
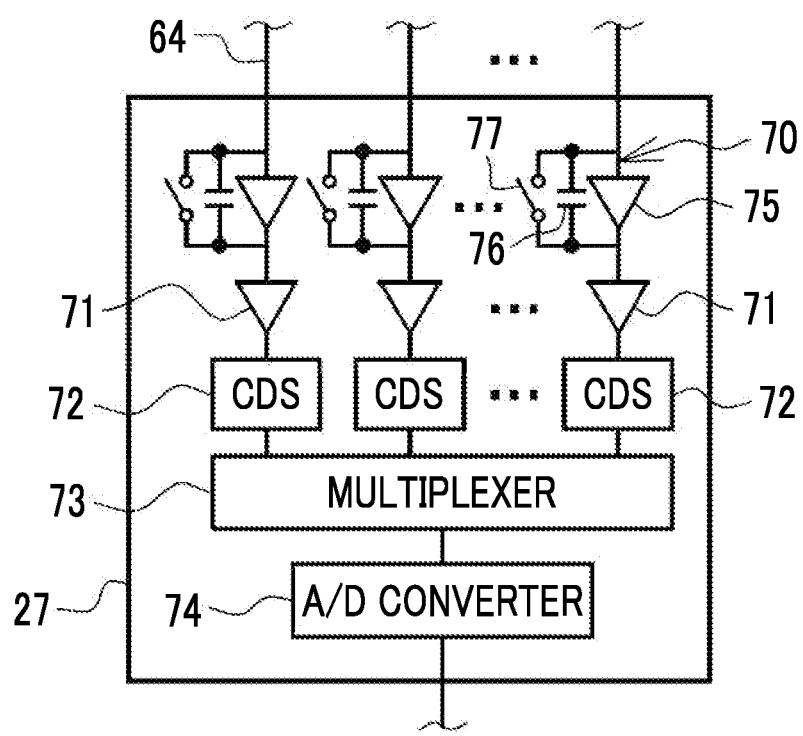
FIG. 10 is a diagram showing a configuration of a readout circuit.

As shown in FIG. 10 as an example, the readout circuit 27 includes a charge amplifier 70, an amplifier 71, a correlated double sampling (CDS) circuit (simply referred to as CDS in FIG. 10) 72, a multiplexer 73, and an analog/digital (A/D) converter 74. One charge amplifier 70, one amplifier 71, and one CDS circuit 72 are provided for each signal line 64. Here, 192 charge amplifiers 70, 192 amplifiers 71, and 192 CDS circuits 72 are provided.

The charge amplifier 70 integrates electric charges input from the signal lines 64, converts the integrated value into an analog voltage signal, and outputs the analog voltage signal. The charge amplifier 70 is composed of an operational amplifier 75, a capacitor 76, and a reset switch 77. The capacitor 76 and the reset switch 77 are connected to each other in parallel between the input terminal and the output terminal of the operational amplifier 75. The input terminal of the operational amplifier 75 is connected to the signal line 64, and the output terminal of the operational amplifier 75 is connected to the amplifier 71.

The output terminal of the operational amplifier 75 for each column is connected to the input side of the multiplexer 73 via the amplifier 71 and the CDS circuit 72. The A/D converter 74 is connected to the output side of the multiplexer 73. The amplifier 71 amplifies the analog voltage signal with a predetermined amplification factor. The CDS circuit 72 removes the reset noise component caused by the reset switch 77 by performing well-known correlated double sampling on the amplified analog voltage signal. The position of the amplifier 71 is not limited to the position between the charge amplifier 70 and the CDS circuit 72, and the amplifier 71 may be provided between the CDS circuit 72 and the A/D converter 74, such as between the CDS circuit 72 and the multiplexer 73.

The multiplexer 73 sequentially selects the connected 192 CDS circuits 72 to sequentially input analog voltage signals, which have been subjected to correlated double sampling, to the A/D converter 74. The A/D converter 74 sequentially converts the analog voltage signals input from the multiplexer 73 into digital signals and outputs the converted digital signals to the readout control circuit 31. The readout control circuit 31 has an image memory for one frame (not shown), and stores the digital signals based on electric charges accumulated in the photoelectric conversion unit 61 of each pixel 60, as a radiation image.

The gate control circuit 30 and the readout control circuit 31 cause the light detection substrate 16 to perform any one of an accumulation operation, an image detection operation, or an electric charge readout operation, and output the radiation image from the light detection substrate 16. The accumulation operation is an operation of causing the photoelectric conversion unit 61 to accumulate electric charges corresponding to the dose of incident radiation. In the accumulation operation, the gate control circuit 30 does not input a gate pulse from the gate drive circuit 25 to the TFT 62 to turn off the TFT 62. Electric charges are accumulated in the photoelectric conversion unit 61 while the TFT 62 is in the off state.

The image detection operation is an operation of detecting, as the radiation image, digital signals based on electric charges accumulated in the photoelectric conversion unit 61 in the accumulation operation. In the image detection operation, the gate control circuit 30 sequentially generates gate pulses from the gate drive circuit 25 to turn on the TFTs 62 in the same row at once, thereby sequentially activating the scanning lines 63 row by row. In a case where the TFTs 62 for one row are turned on, the electric charges accumulated in each of the photoelectric conversion units 61 of the pixels 60 for one row are input to the readout circuit 27 through the signal line 64 of each column. As described above, in the readout circuit 27, the electric charges for one row are converted into analog voltage signals by the charge amplifier 70, and the analog voltage signals are converted into digital signals by the A/D converter 74.

In a case where the analog voltage signals for one row are output from the charge amplifier 70, the readout control circuit 31 turns on the reset switch 77 of the charge amplifier 70. With this, the electric charges accumulated in the capacitor 76 are reset. After the charge amplifier 70 is reset in this way, the gate control circuit 30 causes the gate drive circuit 25 to output gate pulses to the scanning line 63 in the next row, and inputs the electric charges accumulated in the photoelectric conversion units 61 of the pixels 60 in the next row to the readout circuit 27. The gate control circuit 30 and the readout control circuit 31 cause the light detection substrate 16 to repeat such operations, thereby converting the electric charges accumulated in the photoelectric conversion units 61 of the pixels 60 in all rows into digital signals.

The electric charge readout operation is an operation of reading out unnecessary electric charges, such as dark electric charges generated regardless of the presence or absence of irradiation of radiation and residual electric charges resulting from the previous radiation imaging, from the photoelectric conversion unit 61. In this example, the gate control circuit 30 and the readout control circuit 31 perform the electric charge readout operation through a sequential readout method of reading out unnecessary electric charges row by row, as in the image detection operation described above. Specifically, the gate control circuit 30 causes the gate drive circuit 25 to sequentially generate gate pulses to each scanning line 63 row by row, thereby sequentially turning on the TFTs 62 row by row. With this, unnecessary electric charges accumulated in the photoelectric conversion unit 61 are input to the readout circuit 27 through the signal line 64.

The readout control circuit 31 turns on the reset switch 77 of the charge amplifier 70 in synchronization with the generation of the gate pulse to reset unnecessary electric charges. As described above, in the electric charge readout operation, unlike the image detection operation, the conversion of electric charges into analog voltage signals and the conversion of analog voltage signals into digital signals are not performed. Of course, in order to acquire an offset correction image or an afterimage correction image, which will be described later, the conversion of electric charges into analog voltage signals and the conversion of the analog voltage signals into digital signals may be performed in the electric charge readout operation, as in the image detection operation.

The electronic cassette 10 performs various types of correction processing on the radiation image output by the image detection operation. Various types of correction processing include, for example, offset correction processing, afterimage correction processing, sensitivity correction processing, and defective pixel correction processing. The offset correction processing is processing of subtracting an offset correction image detected in a state in which radiation is not emitted, from the radiation image, in a pixel unit. This offset correction processing is performed so that fixed pattern noise caused by dark electric charges or the like is removed from the radiation image. The afterimage correction processing is processing of subtracting an afterimage correction image corresponding to the residual electric charges resulting from the previous radiation imaging, from the radiation image, in a pixel unit. The sensitivity correction processing is processing of correcting variations in the sensitivity of the photoelectric conversion unit 61 of each pixel 60, variations in the output characteristics of the readout circuit 27, and the like, on the basis of sensitivity correction data. The defective pixel correction processing is processing of linearly interpolating the pixel value of the defective pixel with the pixel value of the surrounding normal pixel 60 on the basis of the information on the defective pixel with an abnormal pixel value generated at the time of shipment or periodic inspection. The electronic cassette 10 transmits the radiation image, which has been subjected to various types of correction processing, to an external device, such as a console. Such various types of correction processing may be performed not by the electronic cassette 10 but by the external device.

Next, the action of the above configuration will be described. Power from the power supply circuit 32 is supplied to the gate control circuits 30A and 30B via the power supply terminal 43, the first wiring lines 44A and 44B, and the first power receiving terminals 40A and 40B. Further, power from the power supply circuit 32 is supplied to the readout control circuits 31A and 31B via the power supply terminal 43, the wiring lines 46A and 46B, and the power receiving terminals 42A and 42B. With this, the gate control circuit 30 and the readout control circuit 31 are operated. The gate drive circuit 25 is operated under the control of the gate control circuit 30, and the readout circuit 27 is operated under the control of the readout control circuit 31 so that any one of the accumulation operation, the image detection operation, or the electric charge readout operation is performed on the light detection substrate 16.

In the image detection operation or the electric charge readout operation, gate pulses are sequentially output from the gate drive circuit 25 to the scanning lines 63 row by row. With this, electric charges accumulated in the photoelectric conversion unit 61 of the pixel 60 are input to the readout circuit 27 through the signal line 64. At this time, as shown in FIG. 6, when the gate drive circuits 25 in the upper half are in operation, power supplied from the power supply circuit 32 to the gate control circuit 30B is diverted to the gate control circuit 30A via the second wiring line 45AB. On the contrary, as shown in FIG. 7, when the gate drive circuits 25 in the lower half are in operation, power supplied from the power supply circuit 32 to the gate control circuit 30A is diverted to the gate control circuit 30B via the second wiring line 45AB.

As described above, the electronic cassette 10 has the detection panel 13 (light detection substrate 16) in which the pixels 60 for accumulating electric charges corresponding to radiation are arranged. The electronic cassette 10 comprises the gate control circuits 30A and 30B that control the operations of the gate drive circuits 25, the power supply circuit 32 that supplies power to the gate control circuits 30A and 30B, the first wiring lines 44A and 44B, and the second wiring line 45AB. The first wiring lines 44A and 44B connect the power supply circuit 32 and the gate control circuit 30A, and the power supply circuit 32 and the gate control circuit 30B to each other, and supply the gate control circuits 30A and 30B with power supplied from power supply circuit 32, respectively. The second wiring line 45AB connects the gate control circuits 30A and 30B to each other. Therefore, the power supplied from the power supply circuit 32 to one of the gate control circuits 30A and 30B is diverted to the other through the second wiring line 45AB. The power supplied to one of the gate control circuits 30A and 30B can supplement the power of the other. Therefore, power can be stably supplied to the gate control circuits 30A and 30B.

As shown in FIG. 4 and the like, the gate control circuits 30A and 30B have the first power receiving terminals 40A and 40B, to which the first wiring lines 44A and 44B are connected, and the second power receiving terminals 41A and 41B, to which the second wiring line 45AB is connected, respectively. As shown in FIG. 5 and the like, the first power receiving terminal 40A and the second power receiving terminal 41A, and the first power receiving terminal 40B and the second power receiving terminal 41B are connected to each other in series. Therefore, the power supplied from the power supply circuit 32 to one of the gate control circuits 30A and 30B can be efficiently diverted to the other.

The longer the distance between the power supply circuit 32, and the gate control circuits 30A and 30B is, that is, the longer the length of the first wiring lines 44A and 44B is, the higher the probability of power supply to the gate control circuits 30A and 30B being unstable is due to influences, such as voltage drop caused by wiring resistance. Therefore, in the case of the electronic cassette 10 of which the long side 20 has a length longer than 431.8 mm as in this example, the probability of power supply to the gate control circuits 30A and 30B being unstable increases as compared with an electronic cassette of which the long side 20 has a length of 431.8 mm or less. Therefore, in a case where the technology of the present disclosure is applied to the electronic cassette 10 of which the long side 20 has a length longer than 431.8 mm, the effect of stably supplying power to the gate control circuits 30A and 30B can be exhibited more.

As shown in FIG. 4, the length of one second wiring line 45AB is shorter than the total length of the first wiring lines 44A and 44B. Therefore, the electrical impedance of the second wiring line 45AB is smaller than the total electrical impedance of the first wiring lines 44A and 44B. The influence of the voltage drop caused by the wiring resistance of the second wiring line 45AB can be eliminated as much as possible, and the power supply to the gate control circuits 30A and 30B can be further stabilized.

As shown in FIG. 8, the second wiring line 45AB is directly connected to the gate control circuits 30A and 30B without the connecting component. Therefore, the influence of the voltage drop caused by the resistance of the connecting component can be eliminated, and the power supply to the gate control circuits 30A and 30B can be further stabilized.

In this example, the control circuit is the gate control circuits 30A and 30B that control the operation of the gate drive circuit 25 which applies, to the TFT 62 of the pixel 60, a gate pulse for reading out an electric charge from the pixel 60. In a case where power can be stably supplied to the gate control circuits 30A and 30B, there is no concern of a stepped artifact occurring at the boundary between the upper and lower halves of the radiation image (the middle portion of the rows of the pixels 60). As a result, it is possible to stably output a radiation image with good image quality.

Figure 11:
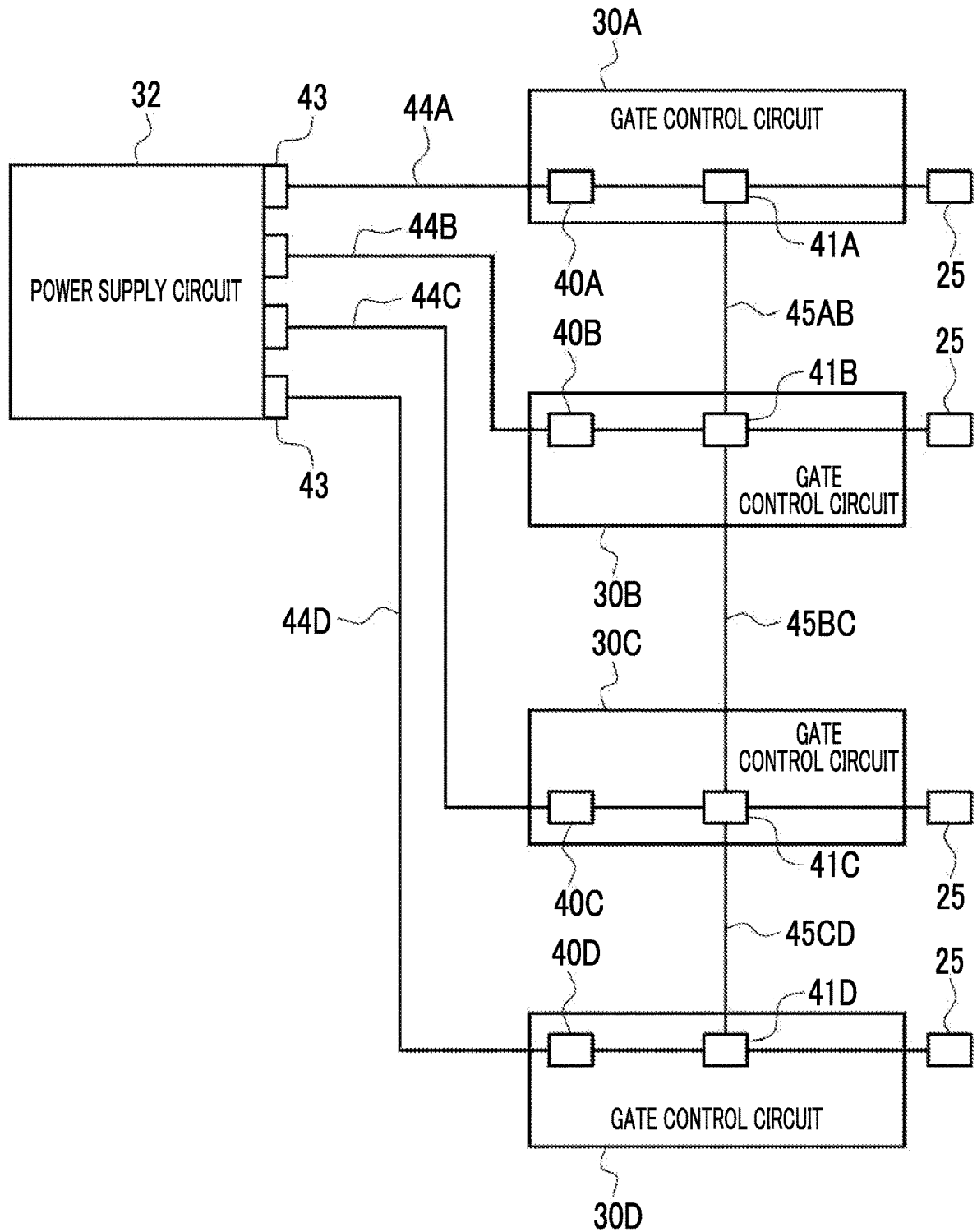
FIG. 11 is a diagram showing another example of the connection relationship between the power supply circuit and the gate control circuit.

The number of gate control circuits 30 is not limited to two shown as an example. As shown in FIG. 11 as an example, four gate control circuits 30A, 30B, 30C, and 30D may share the operation control of the plurality of gate drive circuits 25. In this case, the second power receiving terminal 41B of the gate control circuit 30B and a second power receiving terminal 41C of the gate control circuit 30C are connected to each other by a second wiring line 45BC. Further, the second power receiving terminal 41C of the gate control circuit 30C and a second power receiving terminal 41D of the gate control circuit 30D are connected to each other by a second wiring line 45CD. With this, for example, when the gate control circuit 30A is in operation, power supplied from the power supply circuit 32 to the gate control circuits 30B, 30C, and 30D is diverted to the gate control circuit 30A via the second wiring lines 45AB, 45BC, and 45CD. With this, for example, when the gate control circuit 30C is in operation, power supplied from the power supply circuit 32 to the gate control circuits 30A, 30B, and 30D is diverted to the gate control circuit 30C via the second wiring lines 45AB, 45BC, and 45CD. Reference numerals 40C and 40D indicate first power receiving terminals of the gate control circuits 30C and 30D. Reference numerals 44C and 44D indicate first wiring lines that connect the power supply circuit 32 and the gate control circuit 30C, and the power supply circuit 32 and the gate control circuit 30D to each other, respectively.

In FIG. 11, the gate control circuits 30B and 30C are connected to each other by the second wiring line 45BC, but the second wiring line 45BC may not be provided. In that case, the gate control circuits 30A and 30B may share power supply with each other, and the gate control circuits 30C and 30D may share power supply with each other.

Second Embodiment

Figure 12:
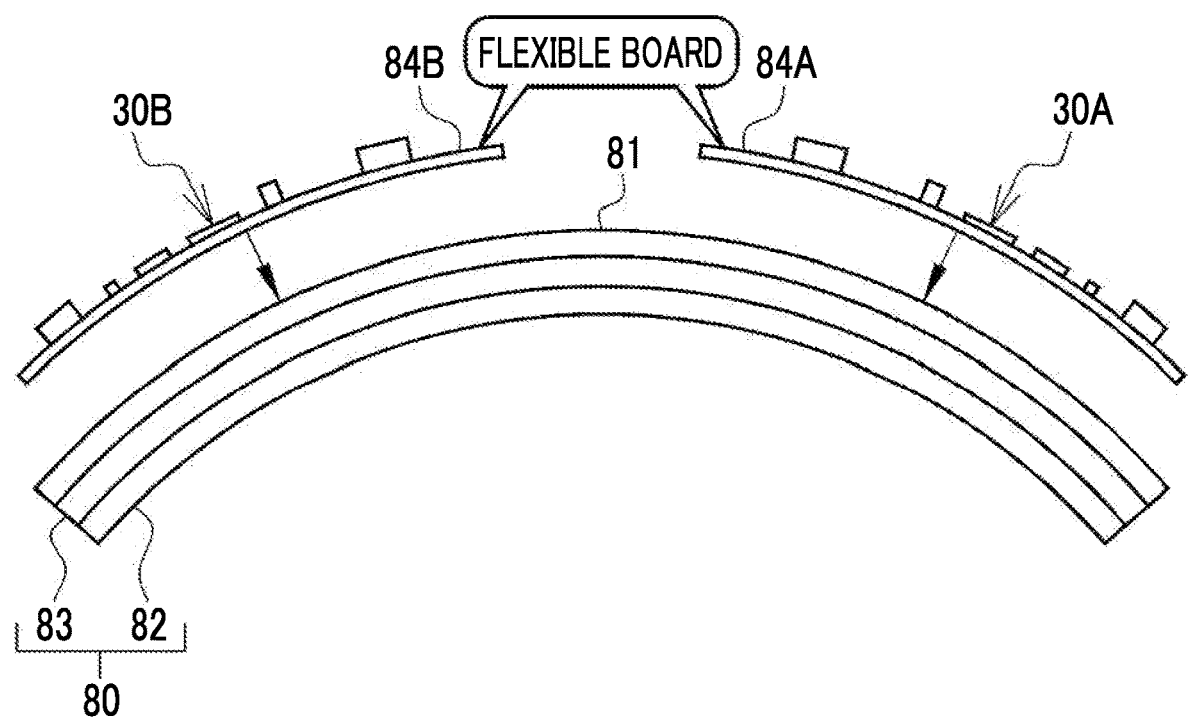
FIG. 12 is a diagram showing a second embodiment in which a detection panel is bent in a circular arc shape.

As shown in FIG. 12 as an example, a detection panel 80 of the second embodiment is attached to a circular arc-shaped base 81. The detection panel 80 is composed of a scintillator 82 and a light detection substrate 83. The scintillator 82 and the light detection substrate 83 are provided on, for example, a flexible thin film sheet made of a resin, such as polyimide, and are bent in a circular arc shape in conformity with the base 81. The circular arc shapes of the detection panel 80 and the base 81 are concave with respect to a radiation source that emits radiation.

In this case, the gate control circuits 30A and 30B are mounted on gate control circuit boards 84A and 84B, which are flexible boards. The gate control circuit boards 84A and 84B are bent in a circular arc shape in conformity with the base 81 and are attached to the back surface of the base 81. Although not shown, the readout control circuits 31A and 31B and the power supply circuit 32 are also mounted on the readout control circuit board, which is a flexible board, and the power supply circuit board, which is a flexible board, respectively. The readout control circuit board and the power supply circuit board are bent in a circular arc shape in conformity with the base 81 and are attached to the back surface of the base 81.

As described above, in the second embodiment, the gate control circuits 30A and 30B are mounted on the gate control circuit boards 84A and 84B, which are flexible boards. Therefore, the technology of the present disclosure can also be applied to a detection panel having a curved surface shape, such as the circular arc-shaped detection panel 80. The curved surface shape of the detection panel is not limited to the circular arc shape, and may be an elliptical arc shape or a bowl shape, such as a parabolic antenna.

In each of the above embodiments, the gate control circuit 30 has been exemplified as the control circuit for which the power from the power supply circuit 32 is diverted to the other control circuit through the connection to the second wiring line 45AB and the like, but the technology of the present disclosure is not limited thereto. Instead of or in addition to the gate control circuit 30, at least two readout control circuits 31 among the plurality of readout control circuits 31 may be connected to each other by at least one second wiring line.

The number of rows and the number of columns of the pixels 60, the number of gate drive circuits 25 and readout circuits 27, the number of rows of the pixels 60 shared by one gate drive circuit 25, and the number of columns of the pixels 60 shared by one readout circuit 27, which are shown above, are merely an example. For example, the number of gate drive circuits 25 may be eight, and the number of rows of the pixels 60 shared by one gate drive circuit 25 may be 240 rows.

The rows of the pixels 60 shared by one gate drive circuit 25 may not be a group of rows obtained by equally dividing the rows of the pixels 60. For example, the number of rows of the pixels 60 shared by a certain gate drive circuit 25 may be 256 rows, and the number of rows of the pixels 60 shared by another gate drive circuit 25 may be 128 rows. Similarly, the columns of the pixels 60 shared by one readout circuit 27 may not be a group of columns obtained by equally dividing the columns of the pixels 60.

In the above first embodiment, the electronic cassette 10 of which the long side 20 has a length longer than 431.8 mm has been exemplified, but the technology of the present disclosure is not limited thereto. An electronic cassette of which one side has a length of less than 431.8 mm may be used.

The electronic cassette has been exemplified as the radiation image detector, but the technology of the present disclosure is not limited thereto. A radiation image detector installed on an imaging table may also be used. Alternatively, a radiation image detector fixed at a position facing the radiation source with a C-arm or the like may be used.

The technology of the present disclosure can also appropriately combine the above-mentioned various embodiments and/or the above-mentioned various modification examples. In addition, it goes without saying that the technology of the present disclosure is not limited to each of the above embodiments and various configurations may be adopted without departing from the gist.

The contents described and shown above are detailed descriptions of parts related to the technology of the present disclosure, and are merely an example of the technology of the present disclosure. For example, the descriptions of the above configurations, functions, operations, and effects are the descriptions of an example of the configurations, functions, operations, and effects of the parts related to the technology of the present disclosure. Accordingly, it goes without saying that unnecessary parts may be deleted, new elements may be added, or replacements may be made with respect to the contents described and shown above, without departing from the gist of the technology of the present disclosure. Further, in order to avoid complications and facilitate understanding of the parts related to the technology of the present disclosure, descriptions of common general knowledge and the like that do not require special descriptions for enabling the implementation of the technology of the present disclosure are omitted, in the contents described and shown above.

In the present specification, "A and/or B" has the same meaning as "at least one of A or B". That is, "A and/or B" means that only A may be used, only B may be used, or a combination of A and B may be used. In addition, in the present specification, the same concept as "A and/or B" is also applied to a case where three or more matters are expressed by "and/or".

All documents, patent applications, and technical standards described in the present specification are incorporated herein by reference to the same extent as a case where each individual document, patent application, and technical standard are specifically and individually stated to be incorporated by reference.

What is claimed is:

1. A radiation image detector comprising:
   a detection panel comprising pixels for accumulating electric charges corresponding to radiation;
   a plurality of control circuits that controls an operation of the detection panel;
   a power supply circuit that supplies power to the plurality of control circuits;
   a plurality of first wiring lines that connects the power supply circuit with the plurality of control circuits, the plurality of first wiring lines being used to supply the plurality of control circuits with the power supplied from the power supply circuit; and
   at least one second wiring line that connects at least two control circuits, among the plurality of control circuits, to each other.

2. The radiation image detector according to claim 1, wherein each control circuit of the plurality of control circuits includes:
   a first power receiving terminal to which one of the plurality of first wiring lines is connected, and
   a second power receiving terminal to which the at least one second wiring line is connected,
   the first power receiving terminal and the second power receiving terminal being connected to each other in series.

3. The radiation image detector according to claim 1, wherein the radiation image detector has a rectangular shape in a plan view and has a long side having a length longer than 431.8 mm.

4. The radiation image detector according to claim 1, wherein a length of the at least one second wiring line is shorter than a total length of the plurality of first wiring lines.

5. The radiation image detector according to claim 1, wherein the at least one second wiring line directly connects the at least two control circuits, among the plurality of control circuits, without a connecting component.

6. The radiation image detector according to claim 1, further comprising:
   a flexible board,
   wherein the plurality of control circuits is mounted on the flexible board.

7. The radiation image detector according to claim 1, wherein each of the plurality of control circuits is a gate control circuit that controls an operation of a gate drive circuit, which applies, to a switching element of each pixel of the pixels, a gate pulse for reading out an electric charge from each pixel of the pixels.

* * * * *